United States Patent [19]
Blechman

[11] Patent Number: 5,334,015
[45] Date of Patent: * Aug. 2, 1994

[54] MAGNETIC ORTHODONTIC APPLIANCE

[76] Inventor: Abraham M. Blechman, 153 Lester Dr., Tappan, N.Y. 10983

[*] Notice: The portion of the term of this patent subsequent to Apr. 27, 2010 has been disclaimed.

[21] Appl. No.: 5,461

[22] Filed: Jan. 4, 1993

Related U.S. Application Data

[63] Continuation-in-part of Ser. No. 887,892, May 26, 1992, abandoned, which is a continuation-in-part of Ser. No. 858,340, Mar. 26, 1992, Pat. No. 5,205,736.

[51] Int. Cl.$^5$ .............................................. A61C 3/00
[52] U.S. Cl. ........................................ 433/18; 433/22
[58] Field of Search .............................. 433/18, 19, 22

[56] References Cited

U.S. PATENT DOCUMENTS

| | | | |
|---|---|---|---|
| 3,353,271 | 11/1967 | Blechman | 433/18 |
| 4,457,707 | 7/1984 | Smiley et al. | 433/18 |
| 4,484,895 | 11/1984 | Smiley et al. | 433/18 |
| 4,508,505 | 4/1985 | Smiley et al. | 433/18 |
| 4,526,539 | 7/1985 | Blechman et al. | 433/18 |
| 4,595,361 | 6/1986 | Blechman et al. | 433/18 |
| 5,066,224 | 11/1991 | Block et al. | 433/18 |

Primary Examiner—John J. Wilson
Attorney, Agent, or Firm—E. Lieberstein

[57] ABSTRACT

An orthodontic appliance for intraorally distalizing teeth without patient compliance, comprising a pair of small complementary permanent magnetic elements, each having a coaxial hole for slidably mounting the magnets on a single common sectional wire, in an arrangement to repel one another, with each element having a protective coating to prevent corrosion and leaching. Additional means are provided for urging the magnetic elements along the sectional wire into predetermined proximity as the molar tooth or teeth distalize. This arrangement avoids undesirable eccentric magnetic movement, maximizes control of the repelling horizontal magnetic forces, and maintains a substantially constant distalizing force without the need for constant readjustment.

15 Claims, 4 Drawing Sheets

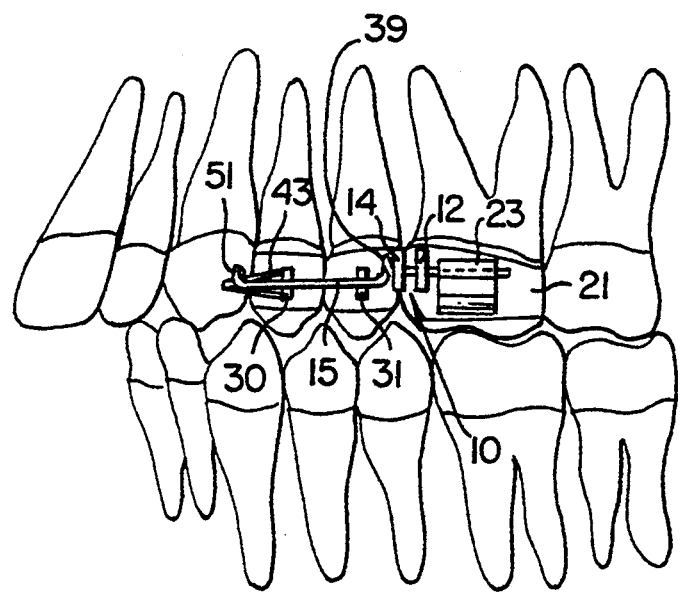
F I G. 1
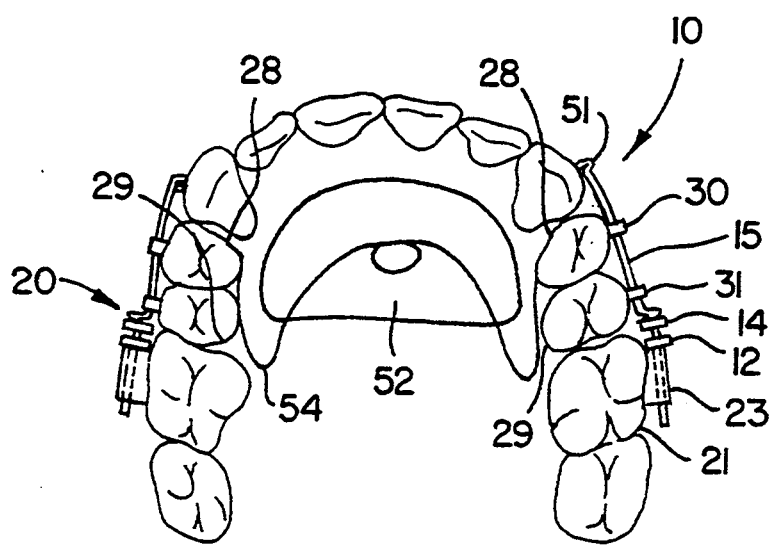
F I G. 5

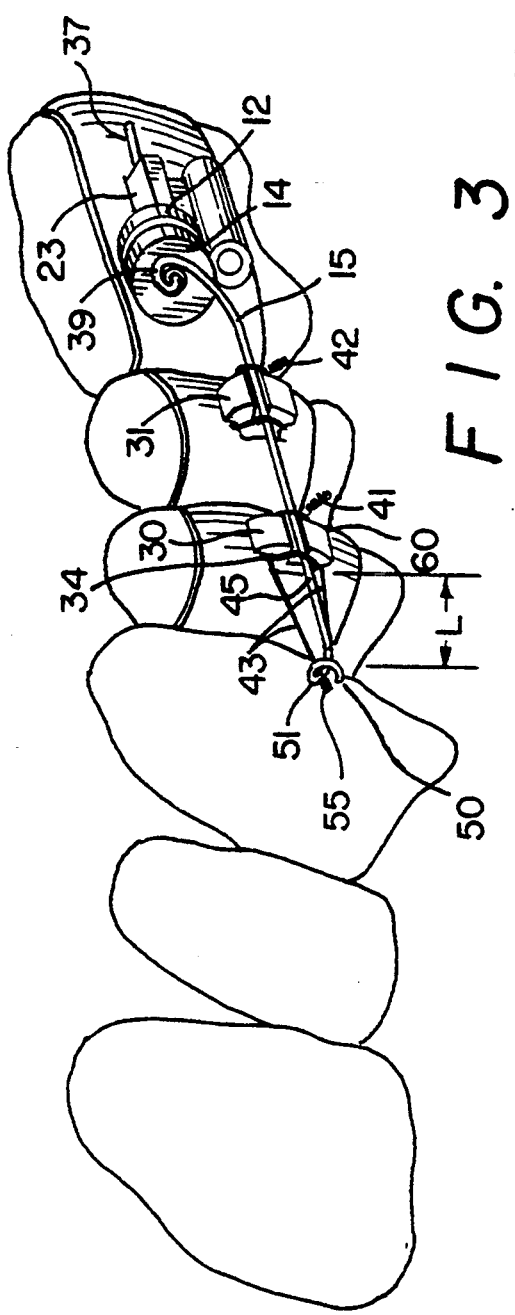
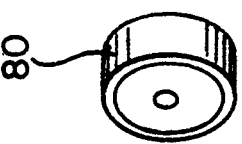
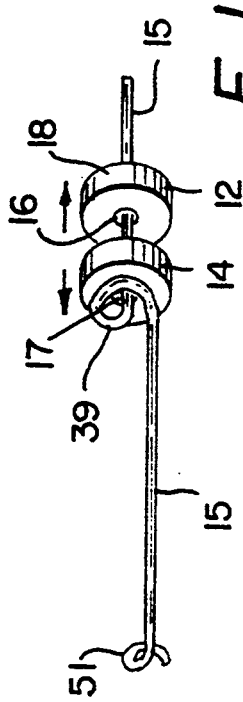
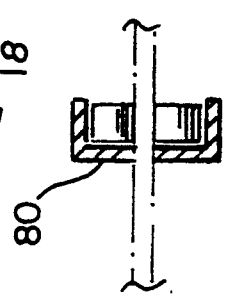

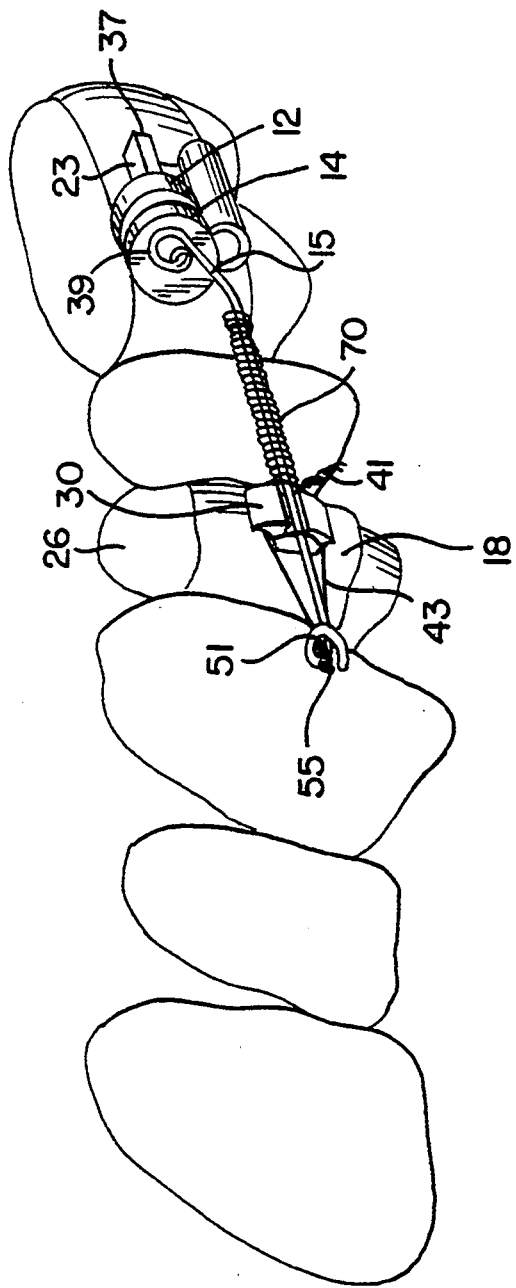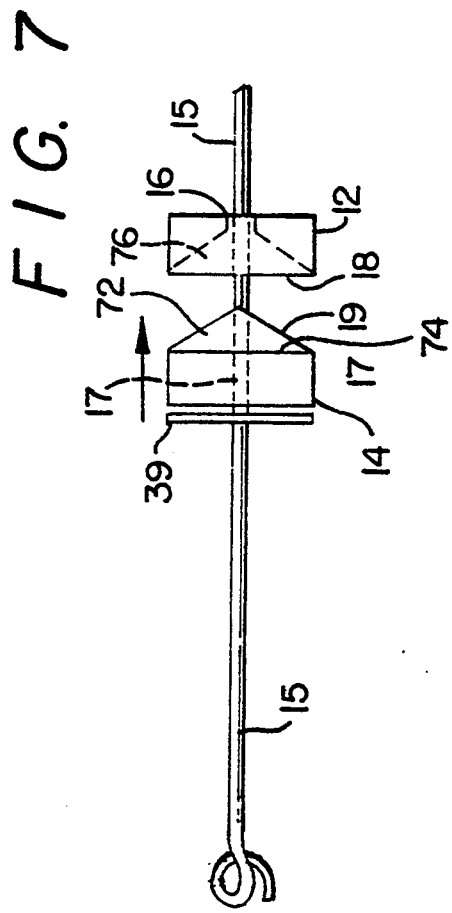
FIG. 6
FIG. 7

MAGNETIC ORTHODONTIC APPLIANCE

FIELD OF THE INVENTION

This application is a continuation-in-part of pending U.S. patent application, Ser. No. 07/887,892, filed May 26, 1992, now abandoned, which in turn is a continuation in part of U.S. patent application, Ser. No. 858,340, filed Mar. 26, 1992, now U.S. Pat. No. 5,205,736 and relates to an orthodontic appliance incorporating magnets to selectively move human dentition intraorally without the need for patient compliance or assistance, and without the need for constant readjustment.

BACKGROUND OF THE INVENTION

Moving teeth intraorally using forces generated from permanent magnets has had little commercial success to date, primarily due to the complexity of conventional permanent magnet appliance systems, their large dimensions, their high cost, and their dependence, at least in part, upon patient compliance, which otherwise results in the patient interfering with the appliance and possibly inactivating or destroying it because of its large dimensions and discomfort. Attachment of a known permanent magnet appliance to the dentition in the upper and lower jaws requires the use of either the main or the sectional arch wires, or both, in an unwieldy arrangement which is difficult to adjust properly and requires patient compliance to avoid inactivation or destruction. The magnetic force developed between the magnetic elements is controlled by bending the wires, to which the elements are connected in a precise way, so that the poles of the magnets are kept aligned to avoid eccentric movement. This has proven to be cumbersome in practice. Moreover, most conventional permanent magnet systems presently in use rely on a rectangular-shaped magnetic element which is encased in a steel sleeve. The sleeve is connected to the sectional wire through a separate fitting, such as, for example, an elongated tube projecting from the steel sleeve. This arrangement inherently results in a physical offset between the center of the magnet and the sectional wire, which creates a rotational bending moment tending to rotate the magnet about the sectional wire. To prevent buccal torquing in such an arrangement and to maintain proper alignment of the poles of the magnetic elements relative to one another, it was necessary to use a sectional wire of rectangular cross-section with a corresponding rectangular fitting, all of which is nonstandard. This resulted in a complex and costly permanent magnet appliance. Other magnetic designs use several large disk-shaped magnets that are uncomfortable, costly, and require considerable patient compliance, resulting in a high degree of non-acceptance.

Because of the recognized clinical advantages of permanent magnet orthodontics, there has been a long-sought need for an orthodontic appliance using small magnets, which can be implemented in a simple, unwieldy, and less costly manner in the treatment of orthodontic cases requiring molar or premolar distalization, which does not depend upon any patient compliance or assistance.

SUMMARY OF THE INVENTION

The orthodontic appliance of the present invention broadly comprises a pair of complementary permanent magnetic elements, each having a cylindrical periphery and an opening axially extending through the symmetrical center thereof, an orthodontic sectional wire having cross-sectional dimensions smaller in size than the opening of each element for slidably mounting said elements along said wire in a mesial and distal relationships, said elements being mounted upon said wire to repel one another and in substantial abutting engagement, with the distal magnetic element abutting the tooth or teeth to be moved distally relative to its proximal teeth, and means for urging the magnetic elements along said common sectional wire into predetermined proximity as movement of the molar tooth or molar teeth occur.

The simplicity of the orthodontic magnetic appliance of the present invention eliminates the need to conjointly use a separate main arch wire on the upper and/or lower jaw, respectively. Moreover, the magnetic appliance may now be readily mounted to the dentition using standard orthodontic mounting brackets, molar tubing, and standard orthodontic wires. Another advantage of the orthodontic appliance of the present invention is its simplicity in moving molar teeth distally on one arch independent of the other arch, or simultaneously on both the upper and lower jaws, respectively. Moreover, the teeth are moved distally without any surgical intervention and without the need for patient compliance or assistance. The orthodontic appliance of the present invention through the use of a coil spring also maintains a substantially constant distalizing force as movement of the molar tooth or teeth occur, thereby avoiding the need for constant readjustment of the appliance. This embodiment of the invention can even accelerate molar distalization beyond its existing rapid rate. This would occur for many reasons, but one of the most important is the combination of a conventional force (coil spring) plus the magnetic field, which can biologically accelerate the rate of bone remodeling as the teeth move.

BRIEF DESCRIPTION OF THE DRAWINGS

Other advantages of the present invention will become apparent from the following detailed description of the invention when read in conjunction with the accompanying drawings of which:

FIG. 1 is an elevational view of the upper and lower jaw of a typical class II human dentition malocclusion viewed from the buccal side, with the orthodontic appliance of the present invention connected to selected posterior teeth in the upper jaw;

FIG. 2 is an exploded view in perspective of the cylindrical magnets of FIG. 1, shown mounted in common on a single sectional wire;

FIG. 3 is an enlarged view of the area in FIG. 1 showing the orthodontic appliance of the present invention mounted to the posterior teeth;

FIG. 5 is an occlusal view of the teeth of the upper jaw of FIG. 1, showing the orthodontic appliance of the present invention symmetrically mounted on opposite sides of the upper jaw in conjunction with an anchorage palatal retainer;

FIG. 6 is a view similar to FIG. 3 using only one bicuspid bracket connection and showing an open coil spring in compression for maintaining the magnets in relative contact;

FIG. 7 is a view in section of an alternative geometry for the cylindrical magnets of FIG. 2;

FIG. 8 is a view similar to FIG. 2, showing one of the cylindrical magnets of FIG. 1 with a protective sleeve;

FIG. 8A shows a variation of the arrangement of FIG. 8, with the protective sleeve covering one of the pole faces of the magnet, except for the central opening; and FIG. 8B is a cross-section of the magnet of FIG. 8A taken along the lines 8—8 of FIG. 8A.

DETAILED DESCRIPTION OF THE INVENTION

Figure 4:
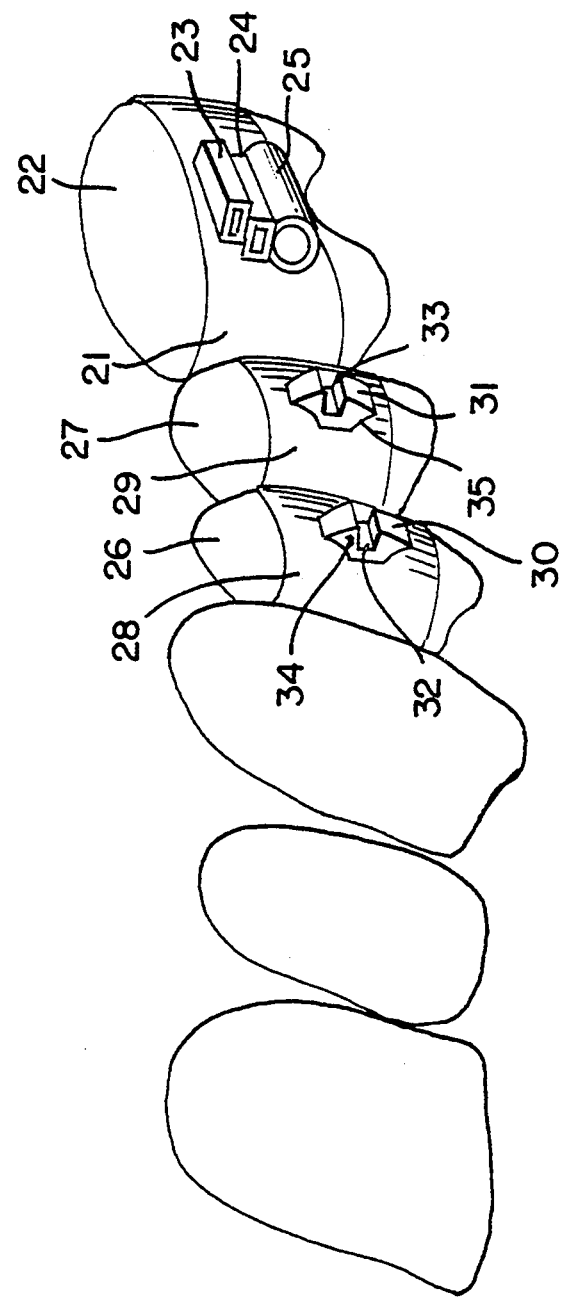
FIG. 4 is another view, similar to FIG. 3, showing the bracket and band connections prior to attachment of the magnet and sectional wire assembly.

Referring to the drawings and, in particular, to FIGS. 1 through 5, inclusive, the orthodontic appliance of the present invention is shown comprising an assembly (10), including a pair of complementary magnetic elements (12) and (14) mounted on a single sectional arch wire (15), in coaxial alignment with the longitudinal axis of the magnetic elements. The sectional wire (15) is a conventional orthodontic, preferably round, steel wire of typically 0.016-inch or 0.018-inch diameter. The magnetic elements (12) and (14) are permanent magnets which have a cylindrical geometry or have a cylindrical periphery, as shown in FIGS. 2 and 3, with an opening (16) and (17), extending through the center of each element along the longitudinal axis thereof. The diameter of each opening (16) and (17) is slightly larger than the diameter of the sectional arch wire (15) to permit the magnets (12) and (14) to freely slide along the arch wire (15). The magnets (12) and (14) are mounted on the arch wire (15) to repel one another, i.e., with their repelling pole faces (18) and (19) abutting one another. The pole faces (18) and (19) may be flat planar surfaces which lie parallel to one another, as is shown in FIG. 2, or may have conical surface geometrics, as will be explained in more detail in connection with the alternative embodiment of FIG. 7. Although the sectional wire (15) is preferably round, other geometries, such as square or rectangular, may be used. If a square sectional wire (15) is used, it is, of course, preferred to use a corresponding geometry for the central openings (16) and (17). Moreover, although the permanent magnetic elements (12) and (14) are cylindrical, they need not be of identical diameter.

The assembly (10) is preferably buccally mounted upon either the upper or lower arch of the teeth on one side thereof, with an equivalent assembly (20), as shown in FIG. 5, symmetrically mounted on the opposite buccal side of the same arch to distalize selected posterior teeth, such as a first molar tooth or first and second molar teeth at the same time or sequentially. The assemblies (10) and (20) can also be mounted and used on the lingual side of the same teeth.

To affix each assembly (10) and (20) to the dentition, it is, at first, necessary to prepare the teeth to receive the assembly by mounting appropriate orthodontic brackets and bands. As shown in FIG. 4, a molar band (21) is fitted upon the first molar tooth (22). The molar band (21) is a commercially available item which can be purchased with edgewise buccal tubes (23) and (24), and a headgear tube (25) which is prewelded to the band (21). It is common for the upper edgewise tube (23) to extend buccally from the band (21). The upper edgewise tube (23) is hollow and is preferably guided by the sectional wire (15) in the operation of the orthodontic appliance of the present invention, as will be hereafter explained in greater detail. The hollow edgewise tube (24) and the hollow headgear tube (25) may remain temporarily nonfunctional and used later in the treatment for other orthodontic purposes independent of this application. The bicuspid teeth (26) and (27) have similar bands (28) and (29) mounted thereon with standard edgewise brackets (30) and (31) prewelded to the bands. The brackets (30) and (31) include slotted openings (32) and (33) adapted to receive the sectional wire (15), and are configured with conventional wings (34) and (35) extending from the openings (32) and (33). The wings (34) and (35) permit the use of conventional ligature wires, Ligature wires, as will be explained hereafter, are used to secure and hold the sectional wire (15) in place within the brackets (30) and (31).

The magnetic elements (12) and (14) are mounted on the sectional wire (15), with the distal end (37) of the sectional wire (15) slidably inserted into the edgewise tube (23). The sectional wire (15) is bent, preferably in advance, to form a loop (39) which secures the mesial side of the magnetic element (14), so the magnetic element (14) is fixed in position mesially, relative to the magnetic element (12). The sectional wire (15) is then inserted into the slotted openings (32) and (33), and ligated to the brackets (30) and (31) using standard ligature wires (41) and (42), respectively. The opposite side (45) of the sectional wire (15), which extends mesially from the brackets (30) and (31), terminates in a free and open end (50). It is preferred to bend the open end (50) of the sectional wire (15) into a loop (51). It is also preferred to wind another ligature wire (43) around the wing (34), and thread this wire through the mesial loop (51), so that the sectional wire (15) is readily movable distally when tightened by the orthodontist, to readily reposition the magnetic elements closer together after they have separated due to the distal movement of the molar tooth or teeth. When the mesial ligature wire (43) through the mesial loop (51) is tightened, it causes the entire sectional wire (15) to slide distally. The bend or loop (39) in the sectional wire (15) pushes the magnetic element (14) back into an active position adjacent to the magnetic element (12). By sliding the sectional wire (15) distally, the edgewise tube (23) now has more guide wire to slide on. This prevents the molar tooth, which is being distalized, from causing the edgewise tube (23) from running off the sectional guide wire (15) and eliminates the need to replace the sectional wire (15) with another wire when reactivating the magnetic appliance. Furthermore, by limiting the magnetic forces to only individual arches, rather than by generating force by the interaction between the upper and lower jaws, avoids the need to prepare the lower jaw with appliances for anchorage, and to use intermaxillary elastics, as is now practiced.

To fully utilize the magnetic force in moving teeth distally, it is advantageous to use an enlarged Nance palatal button (52) as anchorage to prevent anterior movement of all teeth mesial to the molars. The palatal button (52) is connected with a wire (54) to the first and second bicuspid bands (28) and (29) on the lingual side thereof, as well as to the first and second bicuspid bands on the contralateral side. The wire (54) may be secured to the bands (28) and (29) on each side by soldering them together into an integral unit before placement into the mouth. The Nance palatal button (52) provides anchorage to resist the reactive force of the mesial repelling magnetic element in each of the assemblies (10) and (20), respectively.

In the assembled position, the magnetic element (12) abuts the upper edgewise tube (23), and the distal end (37) of the sectional wire (15) projects out only slightly from the distal end of the hollow edgewise tube (23) to prevent irritation of the buccal mucosa. In this position, the magnetic elements (12) and (14) are physically as close to contact as possible, with minimal air gap, so that the magnetic repulsion force between the magnetic elements is at maximum. As the molar tooth (or teeth) distalizes, the edgewise tube (23) moves with the molar teeth distally, guided by the sectional wire (15). After a reasonable displacement occurs between the magnetic elements, the appliance must be reactivated by the orthodontist. As explained earlier, this is accomplished by advancing the entire sectional wire (15) distally simply by tightening the pigtailed free end of the mesial ligature wire running through the mesial loop (51). The latter step is, of course, unnecessary with the embodiment using a coil spring to maintain constant contact.

The dimensions of the magnetic elements (12) and (14), the alloy ingredients, and their energy product will determine the force of repulsion between the magnets. By limiting the thickness of the circular magnetic elements, the correct geometric configuration for force generation is attained, and also the inconvenience of the patient is minimized. The magnetic elements (12) and (14) are preferably composed of a magnetized, stable, high energy product alloy having an axis of polarization coaxial with its longitudinal axis. It is preferred to coat the entire outside surface of each magnetic element (12) and (14), including the hole, with a biocompatible material, such as Parylene-C, manufactured by Union Carbide Corporation, a coating composition of poly-p-xylene with a single chlorine atom replacing a hydrogen atom. The biocompatible coating prevents any alloy ingredients from leaching into the mouth, and also prevents saliva, food, and oxygen from contaminating the magnet. Other biocompatible materials may also be used as a substitute for Parylene-C, or in combination therewith. Such other materials may include acrylic, polycarbonate, nickel electroplating, and titanium nitride. The biocompatible materials prevent corrosion, galvanism, and leaching out of undesirable alloy ingredients. The coating materials must be able to withstand friction while sliding on the sectional wire. This may also prevent galvanic reaction with resultant corrosion. The sectional wire may also be coated to retard corrosion and prevent galvanism. A nickel-titanium wire may also be used.

Because the magnetic elements (12) and (14) are slidably mounted on a common sectional wire (15) along the symmetrical center of each element, the force of repulsion between the opposing pole faces (18) and (19) is essentially unidirectional and parallel to its longitudinal axis. Moreover, eccentric vector forces are canceled out, and no rotational forces exist between the elements to generate torque. Accordingly, the magnetic elements (12) and (14) are limited to unidirectional movement guided by the sectional wire (15). The force of repulsion decreases as the gap between the pole faces increases, in a relationship somewhere between the square of the distance separating the elements and linear. It is, accordingly, necessary to reactivate the elements by incrementally bringing them into closer contact after a predetermined gap separation has developed. The length ("L") of sectional arch wire (15) extending from the mesial edge (60) of the bracket (30) on the first bicuspid to the mesial loop (51) determines the maximum distance of molar distalization (approximately 7 mm). For example, in a full class II malocclusion, approximately 5 mm of molar distalization is required to achieve a class I molar relationship with the lower molar. By overcorrecting, e.g., distalizing 6 mm to 7 ram, the relapse tendency is minimized. This magnetic system is capable of this type of movement. Furthermore, the control of the distal movement of the teeth occurs without any patient assistance or compliance.

As explained above, the embodiment of FIGS. 1-5 requires the appliance to be repeatedly reactivated by the orthodontist following each displacement between the magnetic elements (12) and (14), which corresponds to a reasonable separation. The embodiment of FIG. 6 avoids the necessity of the orthodontist's repeatedly reactivating the appliance in the treatment of the patient. For ease of explanation, the reference numbers which identify corresponding components in FIGS. 1-5 are identical to their counterparts. In the embodiment of FIG. 6, the first bicuspid tooth (26) is shown fitted with a band (28) having an edgewise bracket (30) prewelded to the band (28). The second bicuspid tooth is not fitted with a bracket. The arrangement is otherwise equivalent to the arrangement of FIG. 3, except for the additional use of a compressed open coil spring (70), preferably of a nickel-titanium composition, which is mounted on the sectional wire (15) between the first bicuspid bracket (30) and the bent loop (39) at the mesial side of the magnetic element (14).

A nickel-titanium (NiTi) coil spring (70) is used because NiTi retains a long memory and is capable when in a compressed state of applying a true, uniformly constant force over a relatively long displacement of a molar. This is clearly sufficient for the average maximum displaced distance of 7 mm required for treatment, in accordance with the subject invention. If the active force between the repelling magnets is, e.g., equivalent to 150 grams, then the reactive force of the mesial magnet (14) will be 150 grams. The NiTi coil spring (70) should be compressed to deliver a precalibrated force of 150 grams when fitted in place between the first bicuspid bracket (30) and the bent wire stop (39) adjacent to the mesial magnet (14). Accordingly, the coil spring (70) will urge the mesial magnet (14) distally toward the distal magnet (12), with a substantially constant force despite distal movement of the distal magnet (12) over the entire distance displaced by the distal magnet (12) throughout the molar distalization treatment.

The two magnetic elements (12) and (14) may be maintained in physical contact throughout the treatment or, depending upon the preset spring force maintained at a constant distance apart, i.e., with a constant air gap. Although no reactivation, in theory, is necessary, as a practical matter the orthodontist will inspect the operation and make minor adjustments as is necessary to compensate for minor variations or inaccuracies, if any. Nonetheless, this arrangement permits the moving molar to respond to a true constant force instead of a decaying force, as in the situation when no coil spring is used. The use of a constant force, particularly, with an air gap or no air gap between the magnets, depending on the force chosen, may be more physiologic in treatment, and eliminates the possibility of adverse side effects. The use of an open coil spring in compression avoids the need for incremental readjustments and assures maximum molar distalization by the application of a constant distalizing force.

The amount of force developed between the magnets (12) and (14) depends not only on the geometry of the magnets and their composition, but also on the surface area of the adjacent pole faces (18) and (19). If the surface area of the pole faces (18) and (19) is increased with all other factors being held equal, the force between the magnets will increase. One way of achieving this is shown in FIG. 7. The pole face (19) of the magnetic element (14) is extended to form a three-dimensional convex cone (72) projecting from the cylindrical periphery (74), whereas the opposing pole face (18) of the magnetic element (12) is configured internal of its cylindrical periphery (78) to form a symmetrical concave shape (76). This concave geometry of magnetic element (12) functions as a female receptacle for the male convex projecting cone (72). The convex projecting cone (72) of the magnet (14) should fit into the concave interior of the magnet (12) in a substantially precise manner so that maximum surface contact exists. The pole face surface area is almost doubled with this configuration compared to parallel flat pole faces.

When used with the previously described sectional arch wires to distalize molars, these two magnets are repelling. However, for other orthodontic applications, they can be arranged in attraction.

As explained earlier, the magnets (12) and (14) should be protected with a biocompatible coating material such as Parylene-C. Additional coating materials may include nickel electroplating or titanium nitride. Additional protection may be provided by pressfitting each magnet (12) and (14) into a steel sleeve (80), as shown in FIG. 8. The steel sleeve may be limited to the cylindrical periphery of the magnets (12) and (14), or may also cover a portion of or all of the inactive pole faces of the magnets (82) and (84), respectively, as shown in FIG. 8A. The steel sleeve (80) should be as thin as possible, yet strong enough to prevent chipping and breaking. The edges of the steel sleeve (80) should preferably be rounded. An adhesive such as, for example loctite, may be used in addition to the pressfit.

What is claimed:

1. An orthodontic appliance for distalizing a posterior tooth or teeth without surgical extraction, comprising a plurality of anchoring bands adapted to be mounted to certain selected teeth on a single arch of a patient inclusive of the posterior tooth or teeth to be distalized, and at least one proximal tooth anterior thereto; an edgewise member affixed to the anchoring band on the posterior tooth to be distalized, bracket means affixed to the other band(s); an orthodontic sectional wire extending from said edgewise member to said bracket means; and a pair of permanent magnets, each having a hole axially extending through the symmetrical center thereof, and a protective coating surrounding each magnet and each hole, with said magnets slidably mounted on said sectional wire through said holes in an arrangement to repel one another, with the magnet on the distal side of said sectional wire abutting said edgewise member, and with the other magnet in close proximity thereto, and means for securing said magnet on the mesial side of said sectional wire relative to the proximal tooth or teeth supporting said bracket means.

2. An orthodontic appliance, as claimed in claim 1, wherein said orthodontic sectional wire is of cylindrical geometry, and wherein said opening in each magnet is circular in geometry, with said magnets mounted on said sectional wire so that their longitudinal axes are coaxial.

3. An orthodontic appliance, as claimed in claim 2, wherein said edgewise member is a hollow tube with said sectional wire slidably mounted within said tube.

4. An orthodontic appliance, as claimed in claim 3, wherein each bracket has a slot for receiving said sectional wire.

5. An orthodontic appliance, as claimed in claim 4, further comprising means for ligating said sectional wire to said bracket(s) affixed to the bands on said proximal teeth.

6. An orthodontic appliance, as defined in claim 5, wherein said sectional wire has a bend in the form of a loop for engaging said other magnet on the mesial side thereof to secure said magnet from moving mesially, and with said sectional wire terminating in a mesial free end.

7. An orthodontic appliance, as defined in claim 6, further comprising means for engaging the mesial free end of said sectional wire to enable the sectional wire to be adjusted distally as molar movement occurs.

8. An orthodontic appliance, as defined in claim 7, wherein said mesial free end of said sectional wire is bent in the form of a loop.

9. An orthodontic appliance, as defined in claim 8, further comprising a palatal button and means for connecting said palatal button to said anchoring bands on said proximal tooth or teeth for providing anchorage, to prevent movement of the teeth mesial to the posterior teeth to be distalized.

10. An orthodontic appliance, as defined in claim 5, further comprising spring means for urging said magnetic elements into predetermined proximity with one another, as the posterior tooth is distalized.

11. An orthodontic appliance, as defined in claim 10, wherein said compression spring is composed of nickel-titanium.

12. An orthodontic appliance, as defined in claim 5, wherein each of said permanent magnetic elements has a pole face with a flat planar surface geometry disposed in adjacent proximity to one another.

13. An orthodontic appliance, as defined in claim 5, wherein each of said permanent magnetic elements has a pole face with one pole face of convex geometry extending from the cylindrical periphery, and with the other pole face of concave geometry for intimately receiving the convex pole face.

14. An orthodontic appliance, as defined in claim 5, wherein said protective coating is composed of a material selected from the class consisting of Parylene-C, nickel electroplating, titanium nitride, acrylic, and polycarbonate.

15. An orthodontic appliance, as defined in claim 14, further comprising a steel sleeve surrounding at least the cylindrical periphery of each magnet.

* * * * *